(12) United States Patent
Yamashita

(10) Patent No.: US 9,883,962 B2
(45) Date of Patent: Feb. 6, 2018

(54) STENT DELIVERY SYSTEM

(71) Applicant: TERUMO KABUSHIKI KAISHA, Tokyo (JP)

(72) Inventor: Masao Yamashita, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 325 days.

(21) Appl. No.: 14/327,762

(22) Filed: Jul. 10, 2014

(65) Prior Publication Data
US 2014/0324151 A1    Oct. 30, 2014
US 2017/0216065 A9    Aug. 3, 2017

Related U.S. Application Data

(63) Continuation of application No. PCT/JP2013/052419, filed on Feb. 1, 2013.

(30) Foreign Application Priority Data

Feb. 23, 2012   (JP) ................................. 2012-037463

(51) Int. Cl.
*A61F 2/966*    (2013.01)
*A61F 2/82*    (2013.01)

(52) U.S. Cl.
CPC ............... *A61F 2/966* (2013.01); *A61F 2/82* (2013.01)

(58) Field of Classification Search
CPC .............. A61F 2/966; A61F 2002/9517; A61F 2/95–2/97; A61F 2/2436; A61F 2/1672;
(Continued)

(56) References Cited

U.S. PATENT DOCUMENTS 4,294,254 A * 10/1981 Chamness ........ A61B 17/32056
606/47
4,708,647 A * 11/1987 Pippin .................. A61C 19/043
433/32

(Continued)

FOREIGN PATENT DOCUMENTS

CN   102271627 A   12/2011
JP   H2-271850 A   11/1990
(Continued)

OTHER PUBLICATIONS

International Search Report (PCT/ISA/210) dated May 7, 2013, by the Japanese Patent Office, for International Application No. PCT/JP2013/052419.
(Continued)

*Primary Examiner* — David C Eastwood
*Assistant Examiner* — Charles Wei
(74) *Attorney, Agent, or Firm* — Buchanan Ingersoll & Rooney PC

(57) ABSTRACT

An operating unit constituting a stent delivery system is provided with a first rotary roller having a first gear and a second rotary roller having a second gear. The first gear is meshed with a first tooth portion of a rack member and the second gear is meshed with a second tooth portion of the rack member. The first gear is formed to have a large diameter relative to the second gear and at the time of releasing a stent, after positioning a distal end of an outer tube body close to the stent through the rack member with the rotation of the first rotary roller of the operating unit, it is possible to move the outer tube body toward a proximal side at a lower speed than that in the previous state with the rotation of the second rotary roller.

3 Claims, 10 Drawing Sheets

(58) Field of Classification Search
CPC ...... A61F 2/1667; A61F 2/167; A61F 2/1662; A61F 2002/011; A61M 25/0097; A61M 2025/0681
USPC .................................................. 623/1.11, 1.23
See application file for complete search history.

(56) References Cited

U.S. PATENT DOCUMENTS

| | | | | |
|---|---|---|---|---|
| 6,514,261 | B1* | 2/2003 | Randall | A61F 2/95 604/528 |
| 7,052,511 | B2* | 5/2006 | Weldon | A61F 2/95 606/194 |
| 7,976,574 | B2* | 7/2011 | Papp | A61F 2/95 623/1.11 |
| 7,993,384 | B2* | 8/2011 | Wu | A61F 2/95 623/1.12 |
| 8,343,071 | B2* | 1/2013 | Shabaz | A61B 10/0275 600/566 |
| 8,500,789 | B2* | 8/2013 | Wuebbeling | A61F 2/95 606/108 |
| 8,702,783 | B2 | 4/2014 | Yamashita | |
| 9,149,379 | B2* | 10/2015 | Keady | A61F 2/95 |
| 9,408,592 | B2* | 8/2016 | Shabaz | A61B 10/0275 |
| 2005/0060016 | A1 | 3/2005 | Wu et al. | |
| 2007/0060999 | A1 | 3/2007 | Randall et al. | |
| 2007/0088421 | A1* | 4/2007 | Loewen | A61F 2/95 623/1.11 |
| 2007/0112409 | A1* | 5/2007 | Wu | A61F 2/95 623/1.12 |
| 2007/0191865 | A1* | 8/2007 | Pappas | A61F 2/966 606/108 |
| 2008/0091229 | A1* | 4/2008 | Deyette, Jr. | A61F 2/01 606/194 |
| 2009/0210046 | A1* | 8/2009 | Shumer | A61F 2/95 623/1.11 |
| 2010/0036472 | A1* | 2/2010 | Papp | A61F 2/95 623/1.11 |
| 2012/0253226 | A1* | 10/2012 | Parihar | A61B 10/0275 600/566 |
| 2012/0330401 | A1 | 12/2012 | Sugimoto et al. | |
| 2013/0304187 | A1* | 11/2013 | Yamashita | A61F 2/966 623/1.12 |
| 2015/0051688 | A1* | 2/2015 | Cummins | A61F 2/966 623/1.11 |

FOREIGN PATENT DOCUMENTS

| | | |
|---|---|---|
| JP | 2007-504897 A | 3/2007 |
| JP | 2009-504345 A | 2/2009 |
| WO | 2006/036472 A1 | 4/2006 |
| WO | 2007/022395 A1 | 2/2007 |
| WO | 2007/044929 A1 | 4/2007 |
| WO | 2011/122444 A1 | 10/2011 |

OTHER PUBLICATIONS

Extended European Search Report dated Aug. 21, 2015, by the European Patent Office in corresponding European Patent Application No. 13752063.1-1651. (8 pages).

Office Action (First Office Action) dated Jul. 22, 2015, by the State Intellectual Property Office of China in corresponding Chinese Patent Application No. 201380010522.3, and an English translation of the Office Action. (8 pages).

Office Action (Decision of Refusal) dated May 19, 2017, by the Japanese Patent Office in corresponding Japanese Patent Application No. 2014-500634 and translation (2 pgs).

* cited by examiner

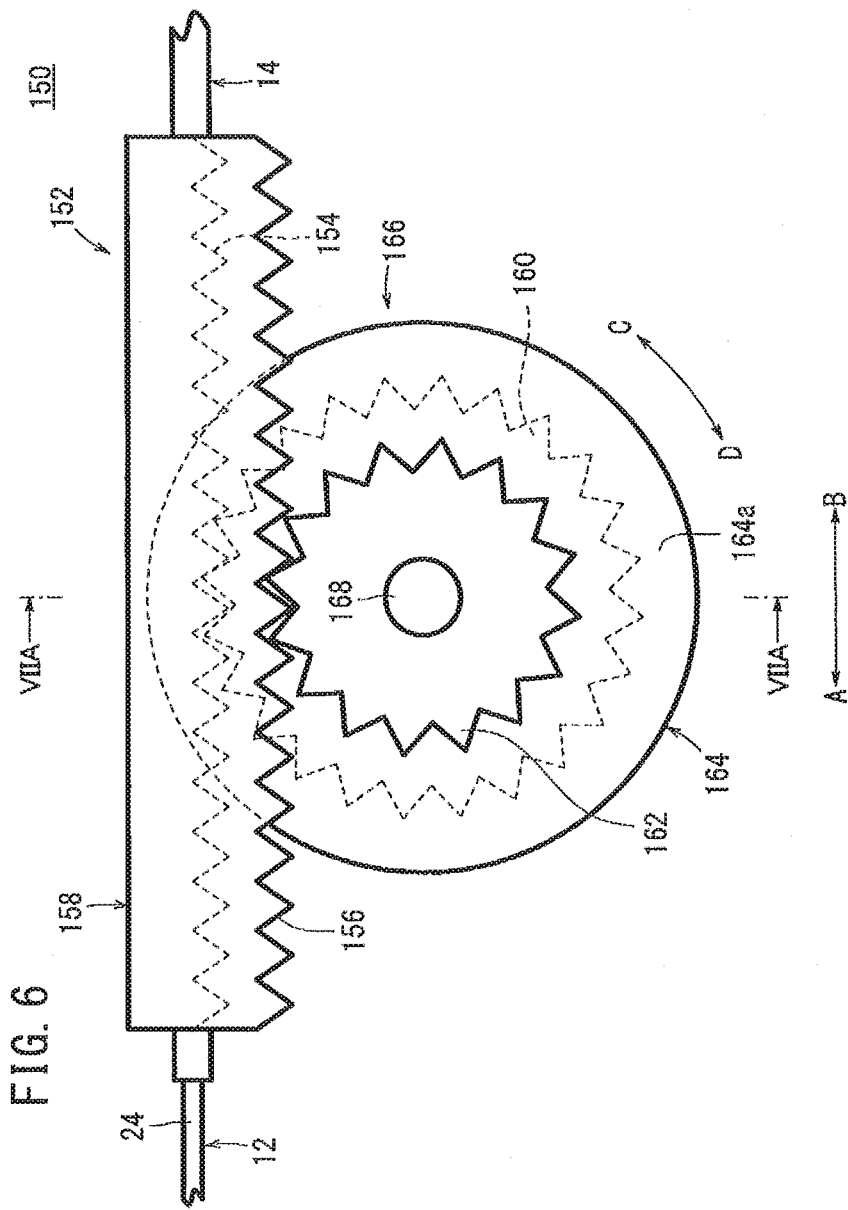

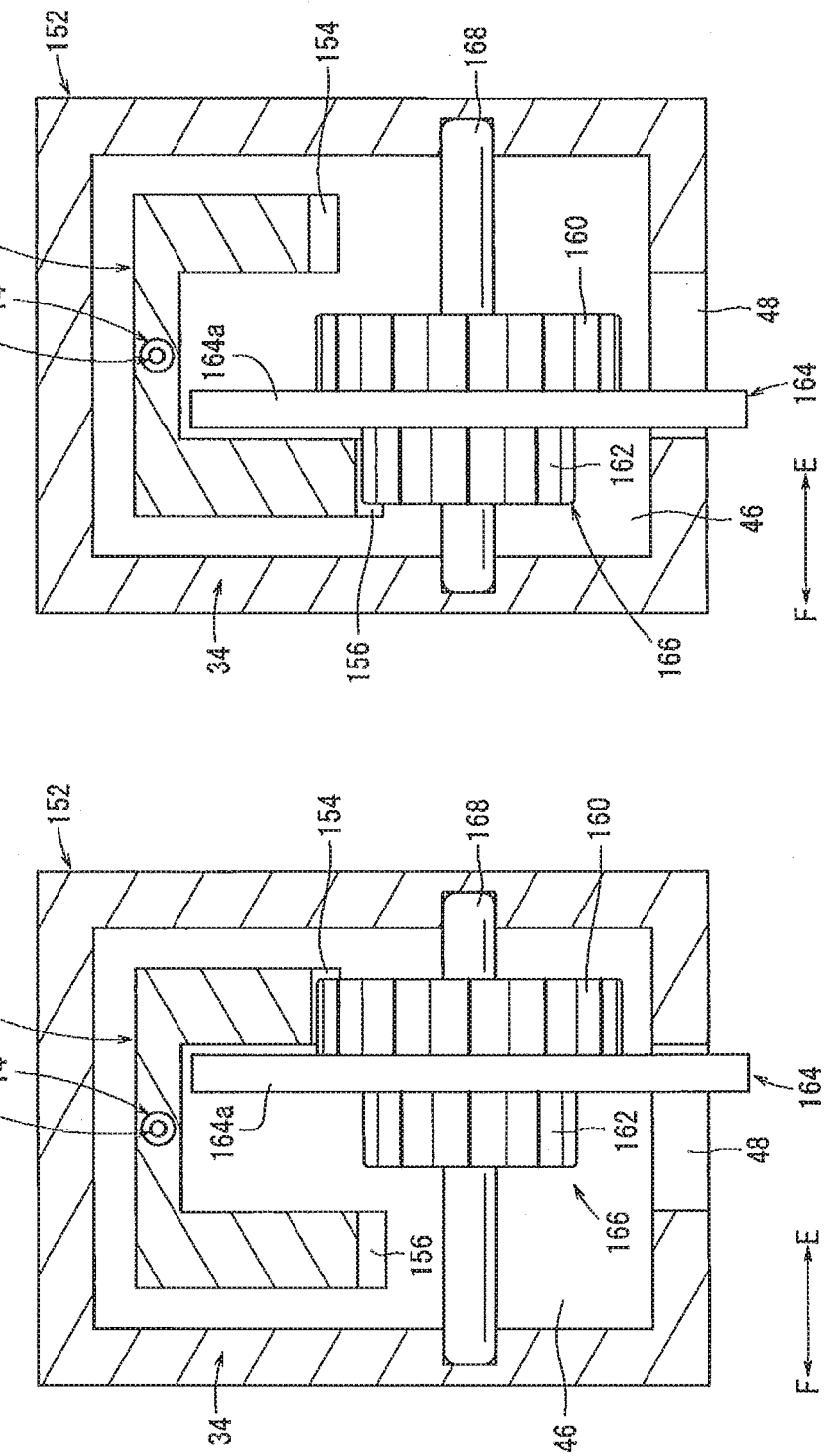

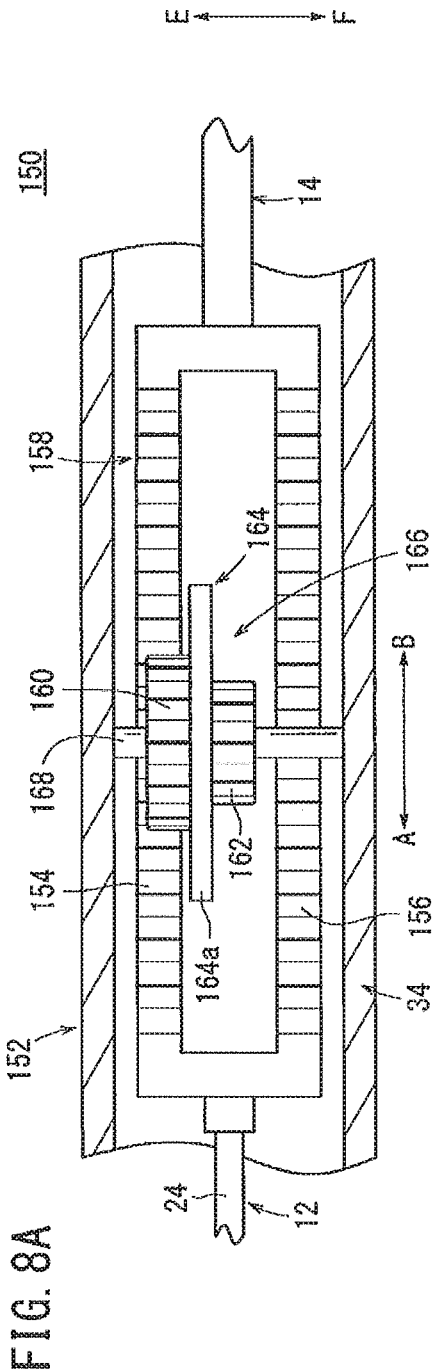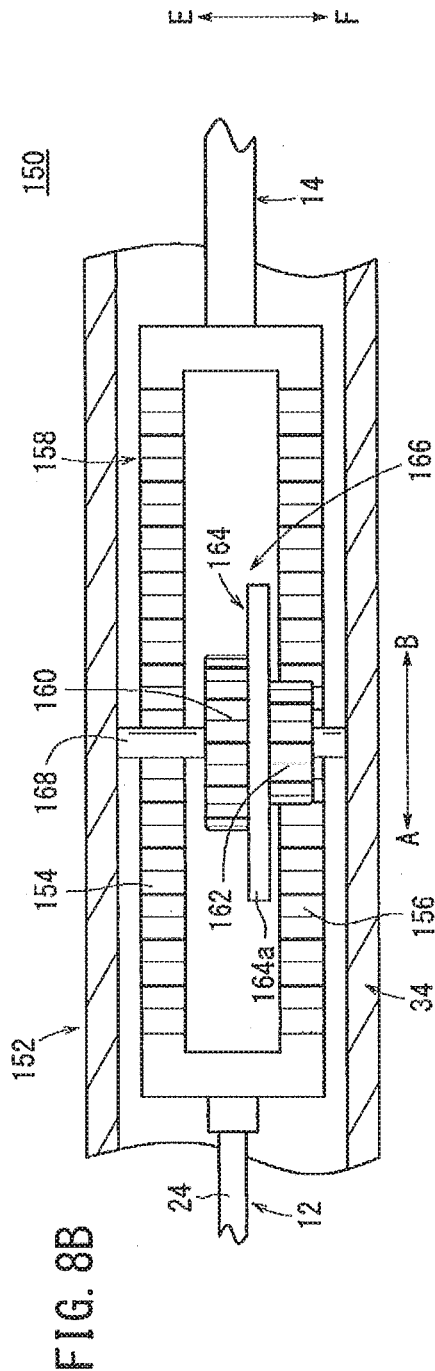

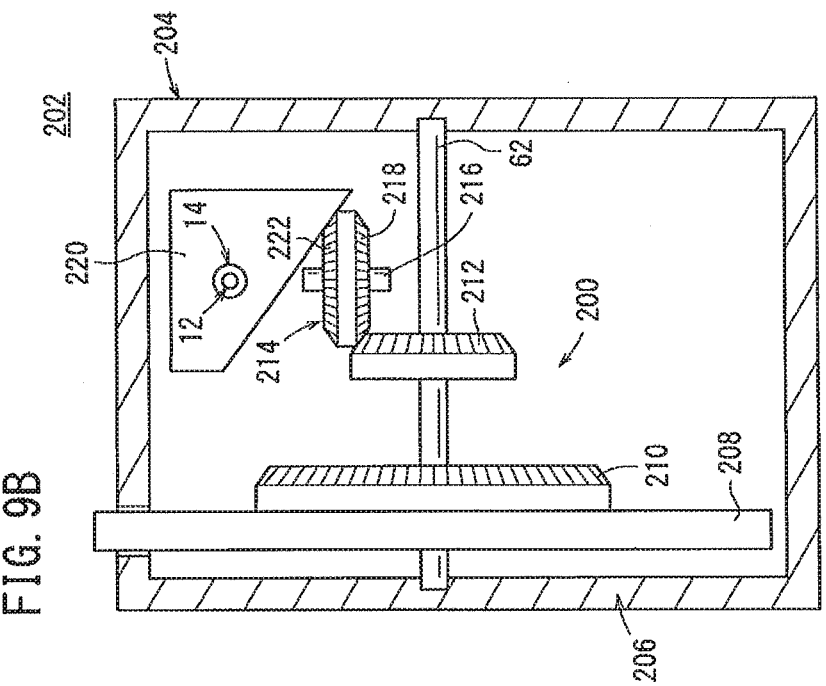
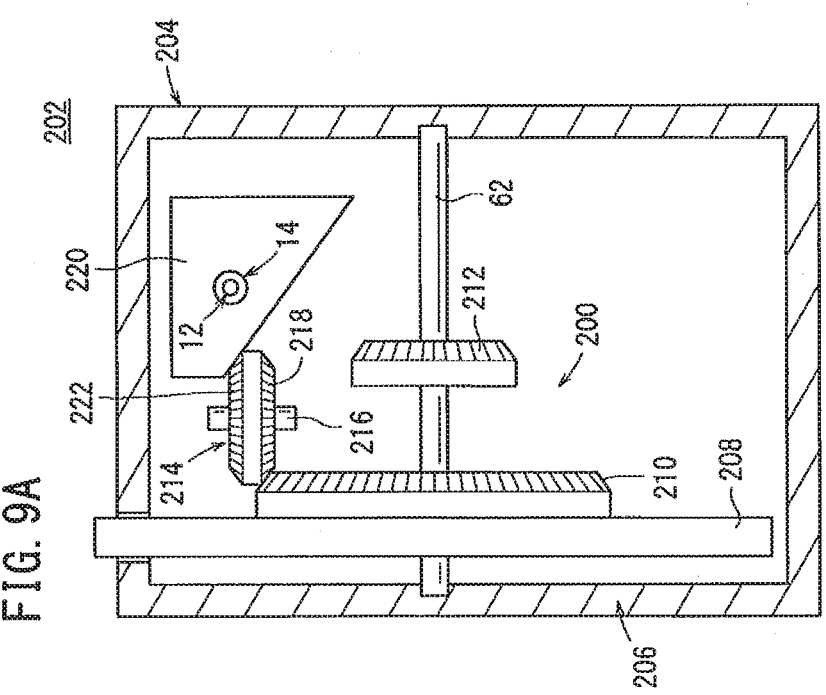

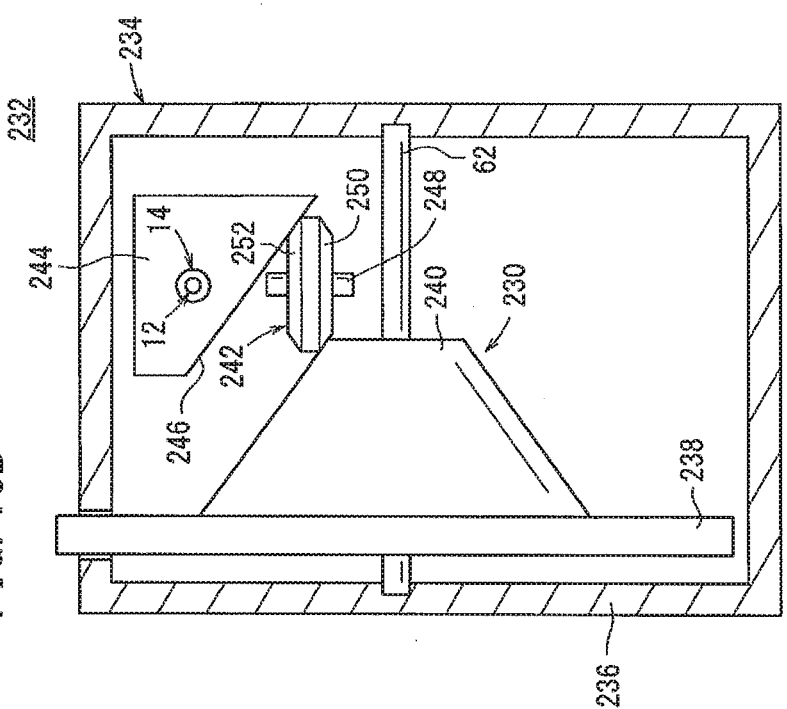
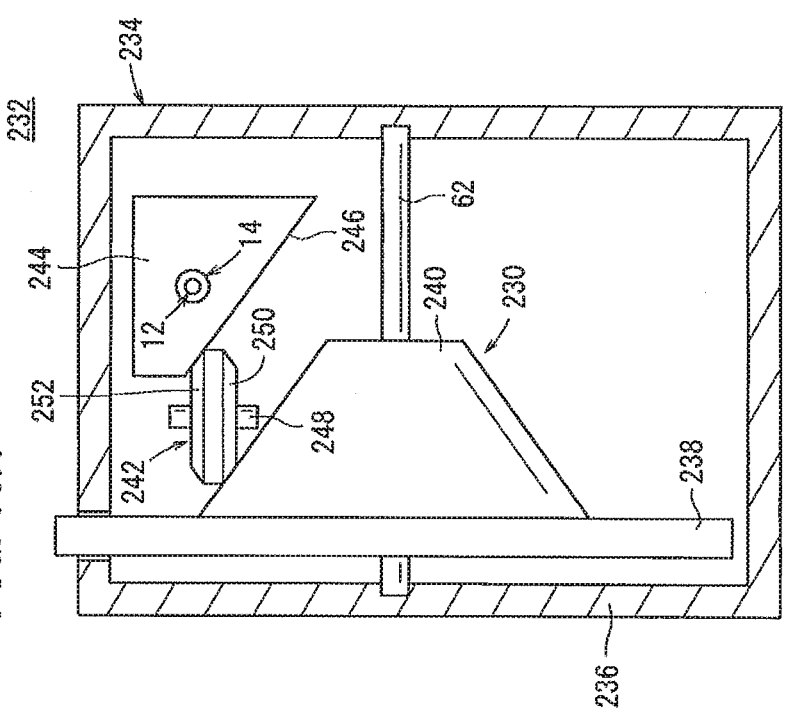

STENT DELIVERY SYSTEM

CROSS REFERENCES TO RELATED APPLICATIONS

This application is a continuation of International Application No. PCT/JP2013/052419 filed on Feb. 1, 2013, and claims priority to Japanese Application No. 2012-037463 filed on Feb. 23, 2012, the entire content of both of which is incorporated herein by reference.

TECHNICAL FIELD

The present application relates to a stent delivery system for delivering and indwelling a stent into a lumen of a living body such as a blood vessel.

BACKGROUND DISCUSSION

Conventionally, there have been cases where a stent, which is formed in the shape of a hollow cylinder having a multiplicity of openings in its side wall from a metallic wire or the like, to be expanded in a lumen of a living body, such as a blood vessel, bile duct, trachea, esophagus and urethra, is used for improvement of a stenosed part or an obstructed part generated in the lumen of the living body.

In connection with the case of a self-expandable stent in which the stent itself has a self-expanding function, for example, there has been known a stent delivery system in which the stent is delivered into a lumen of a living body in the state of being compressed and contained in a gap between an inner tube and an outer tube, and then the outer tube is retracted proximally so as to release the stent, whereby the stent is put indwelling in a desired part in the lumen.

As disclosed in JP-T-2007-504897, for example, the above-mentioned stent delivery system has an operating mechanism for moving the outer tube in an axial direction relative to the inner tube. In the operating mechanism, a gear rack is meshed with a gear of a rotatable wheel, and the outer tube is configured to be connected to an end portion of the gear rack. With the wheel rotated in a predetermined direction, the gear rack is advanced and retracted in the axial direction so as to move the outer tube relative to the inner tube, whereby the stent is released to the exterior of the outer tube.

SUMMARY

At the time of releasing a stent, an outer tube and a gear rack are promptly moved until a distal end of the outer tube reaches the vicinity of the stent, and meanwhile, the outer tube and the gear rack are moved at a low speed, thereby accurately performing the release of the stent after the distal end of the outer tube reaches the vicinity of the stent.

A stent delivery system by which release of a stent can be performed promptly and accurately is provided.

A stent delivery system includes: an inner tube; a stent which is compressed toward a center axis and disposed on a distal side of the inner tube at the time of insertion into a lumen of a living body, and which can be restored into its pre-compression shape by expanding outward when put indwelling in the lumen of the living body; an outer tube which is disposed on an outer surface side of the inner tube, can contain the stent in its lumen, and can release the stent to the exterior by moving proximally relative to the inner tube; and an operating unit for moving the outer tube in an axial direction relative to the inner tube. The operating unit includes a rotary body which is rotated by an operation performed by an operator, a displacement body which is connected to the outer tube and is provided so as to be movable in the axial direction, and a speed change mechanism which is provided between the rotary body and the displacement body and changes the speed of the rotation of the rotary body, thereby changing the moving speed of the displacement body by transmitting the rotation to the displacement body. The speed change mechanism includes a speed change portion which is rotated together with the rotary body and of which the diameter is changed continuously or gradually along rotary shafts of the rotary body, and a transmission portion which is provided on the displacement body and which is meshed with or is in sliding contact with the speed change portion.

With the provision of the speed change mechanism between the rotary body and the displacement body in the operating unit, the speed change mechanism changing the speed of the rotation of the rotary body, thereby changing the moving speed of the displacement body by transmitting the rotation to the displacement body, it is possible to change the moving speed of the outer tube until a distal end of the outer tube reaches the vicinity of the stent at the time of releasing the stent by moving the outer tube relative to the inner tube into the moving speed of the outer tube after the distal end of the outer tube reaches the vicinity of the stent. As a result, it is possible to release the stent promptly and accurately in the stent delivery system.

BRIEF DESCRIPTION OF THE DRAWINGS

FIG. 6 is a schematic block diagram of a speed change mechanism used in an operating unit in a stent delivery system according to a third embodiment representing another example of the stent delivery system disclosed here.

FIG. 7A is a cross-sectional view taken along line VIIA-VIIA of FIG. 6 and FIG. 7B is a cross-sectional view showing a state in which a rotary roller shown in FIG. 7A is moved toward the other end portion side of a rack member and is meshed with a second tooth portion.

FIG. 8A is a plan view of the operating unit shown in FIG. 7A seen from below and FIG. 8B is a plan view of the operating unit shown in FIG. 7B seen from a lower surface.

FIG. 9A is a schematic block diagram showing an operating unit of a stent delivery system to which is applied a speed change mechanism according to a further embodiment representing an example of the stent delivery system disclosed here and FIG. 9B is a schematic block diagram showing a state in which meshing of a transmission gear is switched from a first gear to a second gear in the speed change mechanism of FIG. 9A.

FIG. 10A is a schematic block diagram showing an operating unit of a stent delivery system to which is applied a speed change mechanism according to a further embodiment representing another example of the stent delivery system disclosed here and FIG. 10B is a schematic block diagram showing a state in which a transmission pulley is moved in a direction away from a rotary roller in the speed change mechanism of FIG. 10A.

DETAILED DESCRIPTION

Figure 1:
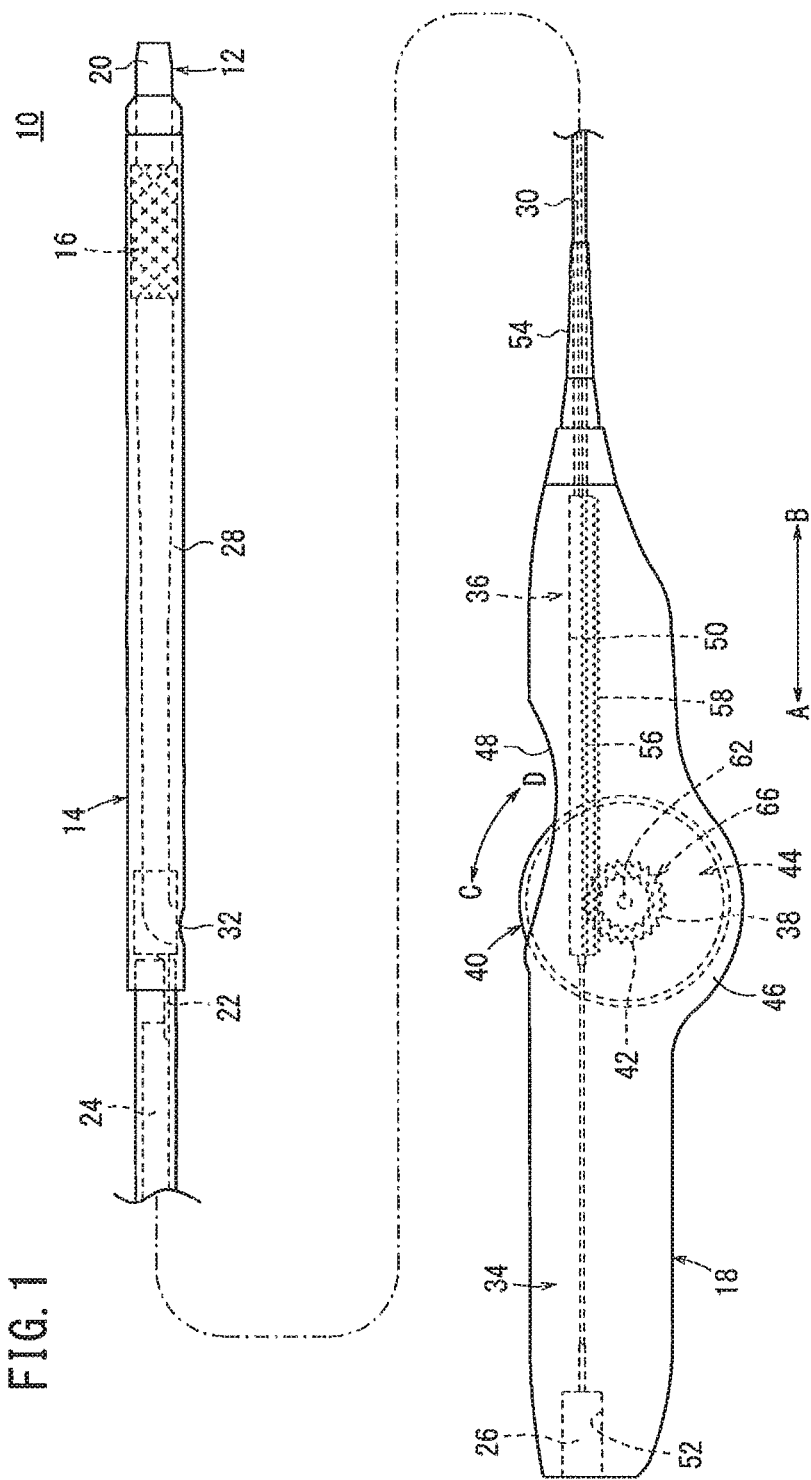
FIG. 1 is a general configuration view of a first embodiment of the stent delivery system representing an example of the stent delivery system disclosed here.

As shown in FIG. 1, this stent delivery system 10 includes: an inner tube body (inner tube) 12 having a tubular shape; an outer tube body (outer tube) 14 disposed on the outer circumference side of the inner tube body 12; an expandable stent 16 contained (located) between the inner tube body 12 and the outer tube body 14; and an operating unit 18 for moving the outer tube body 14 relative to the inner tube body 12.

In FIG. 1, the left side of the inner tube body 12 and the outer tube body 14 is referred to as a "proximal end (rear end)" side (direction of arrow A), and the right side of the inner tube body 12 and the outer tube body 14 is referred to as a "distal end" side (direction of arrow B), the same applying also to the other figures. The direction from the proximal end of the outer tube body 14 (or the inner tube body 12) may be referred to as the axial dimension of the outer tube body 14 (or the inner tube body 12).

As shown in FIG. 1, the inner tube body 12 includes: a first distal tube 20 with a guide wire lumen where a guide wire is inserted into and passes through; a first proximal tube 24 connected through a connecting member 22 to the proximal side (the direction of arrow A) of the first distal tube 20; and a connector 26 connected to the proximal end of the first proximal tube 24.

This inner tube body 12 is composed of tubular bodies, in which the distal ends and proximal ends of the first distal tube 20 and the first proximal tube 24 are respectively open, and the distal end of the first distal tube 20 is disposed so as to protrude beyond the distal end of the outer tube body 14. The above-mentioned guide wire is used, for example, for guiding the stent delivery system 10 to a lesion in a lumen of a living body.

The inner tube body 12 has a structure in which the proximal end of the first distal tube 20 and the distal end of the first proximal tube 24 are connected to each other, through the connecting member 22, inside the outer tube body 14. In addition, the first proximal tube 24 has a lumen penetrating through the first proximal tube 24 from the distal end to the proximal end of the first proximal tube 24. A liquid such as physiological saline is injected into the lumen via the connector 26.

The outer tube body 14 is composed of tubular bodies and has a second distal tube 28 in which the first distal tube 20 of the inner tube body 12 is disposed and a second proximal tube 30 which is connected to the proximal side (the direction of arrow A) of the second distal tube 28 and in which the first proximal tube 24 is disposed.

The distal end of the second distal tube 28 functions as a release port at the time of indwelling the stent 16 into a lesion in a lumen of a living body, and functions also as a containing port at the time of containing the stent 16 again, having been released to an intermediate extent.

In addition, on the proximal end of the second distal tube 28, there is a guide wire leading-out hole 32 opened so as to establish communication between the inner lumen of the second distal tube 28 and the exterior. The guide wire leading-out hole is provided such that it can communicate with the opening of the guide wire lumen of the first distal tube 20 provided inside the second distal tube. Through the guide wire leading-out hole 32, the guide wire is inserted into and passes through (positioned in) the guide wire lumen of the inner tube body 12.

The stent 16 is a substantially cylindrical shaped mesh having a multiplicity (plurality) of openings. The stent 16 is a self-expandable stent which is disposed between the second distal tube 28 of the outer tube body 14 and the first distal tube 20 of the inner tube body 12 in the state of being compressed radially inward toward the center axis at the time of insertion into a lumen of a living body, and which, by being released via the distal end of the outer tube body 14 into a lesion in the lumen of the living body, can be expanded radially outward to be restored into its pre-compression shape.

Figure 2:
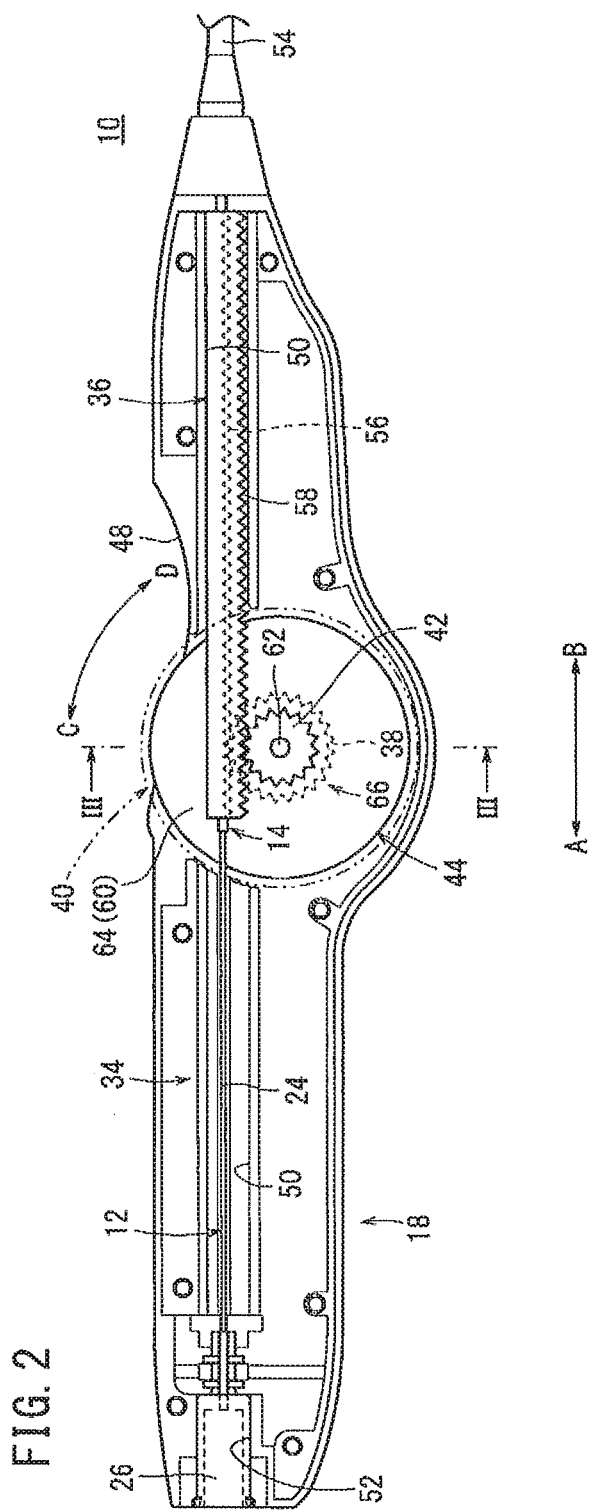
FIG. 2 is a side view of the inside of an operating unit shown in FIG. 1.
Figure 3:
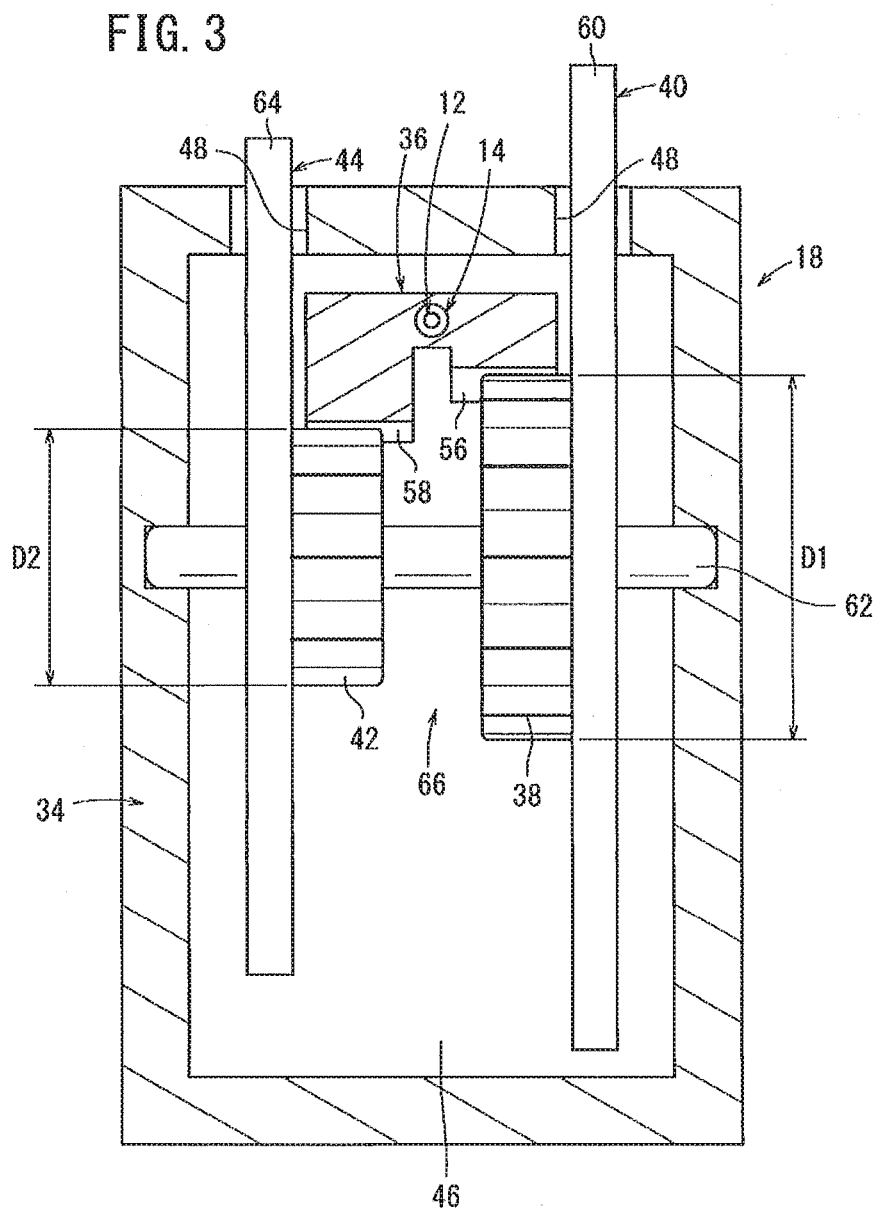
FIG. 3 is a cross-sectional view taken along line III-III of FIG. 2.

As shown in FIGS. 1 to 3, the operating unit 18 includes: a housing 34; a rack member (displacement body) 36 contained inside the housing 34 and connected to the outer tube body 14; a first rotary roller (rotary body) 40 which has a first gear (speed change portion) 38 meshed with the rack member 36; and a second rotary roller (rotary body) 44 which has a second gear (speed change portion) 42 meshed with the rack member 36.

The housing 34 has a round shape at its central portion. A roller containing section 46 capable of containing the first and second rotary rollers 40 and 44 is formed (disposed) in the substantially central portion of the housing. Part of the first and second rotary rollers 40 and 44 is exposed to the exterior through a roller hole 48 formed (provided) in the roller containing section 46.

In addition, the housing 34 houses a set of containing grooves 50 in which the rack member 36 is contained and retained so as to be movable in the axial direction (in the directions of arrows A and B). A connector containing section 52 containing the connector 26 is formed (provided) on the proximal side (in the direction of arrow A) of the containing groove 50. Moreover, the connector 26 is fixed to the housing 34 by being contained in the connector containing section 52. As a result, the proximal end of the first proximal tube 24 constituting the inner tube body 12 is fixed to the operating unit 18 through the connector 26.

Meanwhile, a distal nozzle 54, by which the second proximal tube 30 of the outer tube body 14 is slidably retained, is mounted on the distal end of the housing 34. The distal nozzle 54 includes a through-hole (not shown) where the second proximal tube 30 is inserted into and passes through (positioned in).

The rack member 36 is composed of blocks which are formed in straight shapes. The proximal end of the second proximal tube 30 of the outer tube body 14 is fixed by being inserted into and passing through the rack member. In this case, the inner tube body 12 is movable inside the outer tube body 14.

Then, the rack member 36 is inserted into the containing groove 50 inside the housing 34, whereby the rack member is retained in the state of being rectilinearly movable toward the distal side and the proximal side (in the directions of arrows A and B) of the housing 34.

In addition, a lower surface of the rack member 36 is provided inside the housing 34 so as to face a shaft 62 which is supported such that the first and second rotary rollers 40 and 44 are rotatable. Moreover, a part which is the first rotary roller 40 side on the lower surface of the rack member 36 is provided with a plurality of first tooth portions (transmission portions) 56 defined by projections and recesses arranged along the axial direction (in the directions of arrows A and B) and a part which is the second rotary roller 44 side is provided with a plurality of second tooth portions (transmission portions) 58 defined by projections and recesses arranged along the axial direction (in the directions of arrows A and B).

The first and second tooth portions 56 and 58 have an identical pitch along the axial direction (in the directions of arrows A and B) of the rack member 36 and the second tooth portion 58 is provided downward relative to the first tooth portion 56 so as to be substantially parallel to the first tooth portion 56.

That is, as shown in FIG. 3, the lower surface of the rack member 36 includes a part having the first tooth portion 56 and a part having the second tooth portion 58 that are in a stepped shape having different heights.

The first rotary roller 40 includes, for example, a main body portion 60 formed in a disk shape and a first gear 38 which protrudes sideways from the central portion of the main body portion 60 and the first rotary roller is rotatably provided in the housing 34 through a shaft 62 which is inserted into and passes through (positioned in) the center of the main body portion 60 and the first gear 38.

The first gear 38 includes a plurality of gear teeth along the outer circumferential surface which is formed with a predetermined diameter and is meshed with the first tooth portion 56 of the rack member 36. With the first rotary roller 40 rotated, the rack member 36 is moved rectilinearly along the containing groove 50. In addition, part of the main body portion 60 of the first rotary roller 40 is exposed to the exterior through the roller hole 48 of the housing 34 and the operator rotates the first rotary roller 40 through the exposed main body portion 60.

The second rotary roller 44 includes, for example, a main body portion 64 formed in a disk shape and a second gear 42 which protrudes sideways from the central portion of the main body portion 64 and the second rotary roller is rotatably provided in the housing 34 through a shaft 62 which is inserted into and passes through (positioned in) the center of the main body portion 64 and the second gear 42. In addition, the second rotary roller 44 is provided coaxially with the first rotary roller 40 through the shaft 62 and the second gear 42 of the second rotary roller 44 is provided so as to face the first gear 38. Part of the main body portion 64 of the second rotary roller 44 is exposed to the exterior through the roller hole 48 of the housing 34 and the operator rotates the second rotary roller 44 through the exposed main body portion 64.

Since the main body portion 64 of the second rotary roller 44 has a small diameter relative to the main body portion 60 of the first rotary roller 40, as shown in FIG. 3, the amount protruding to the exterior through the roller hole 48 is different from that of the first rotary roller 40. For this reason, when the operator operates the first and second rotary rollers 40 and 44, it is possible to select either one of the rotary rollers by sensory identification of both the rollers. Furthermore, for clear identification of the first rotary roller 40 and the second rotary roller 44 by the operator, for example, both the rollers may be respectively colored with different colors.

The second gear 42 includes a plurality of gear teeth along the outer circumferential surface which is formed to have a smaller diameter than the first gear 38 and is meshed with the second tooth portion 58 of the rack member 36. Specifically, a diameter D2 of the second gear 42 (for example, the tooth tip diameter) is set to be small relative to a diameter D1 of the first gear 38 (for example, the tooth tip diameter) (D2<D1). As a result, the number of teeth of the second gear 42 is small relative to the number of teeth of the first gear 38.

That is, in the housing 34, the first rotary roller 40 is disposed at a position where the first gear 38 faces the first tooth portion 56 of the rack member 36 and the second rotary roller 44 is disposed at a position where the second gear 42 faces the second tooth portion 58 of the rack member 36.

Moreover, with the second rotary roller 44 rotated, the rack member 36 rectilinearly moves along the containing groove 50. In this instance, since the number of teeth of the second gear 42 is small relative to the number of teeth of the first gear 38, when the second rotary roller 44 is rotated at a rotation speed (rotation angle) the same as that of the first rotary roller 40, the distance moved along the axial direction (in the directions of arrows A and B) of the rack member 36 becomes small.

In other words, when the second rotary roller 44 is rotated at a rotation speed (rotation angle) the same as that of the first rotary roller 40, the moving speed of the rack member 36 becomes relatively slow.

The first rotary roller 40 having the first gear 38 and the second rotary roller 44 having the second gear 42 function as the speed change mechanism 66 which can change the moving speed along the axial direction (in the directions of arrows A and B) of the rack member 36. The speed change mechanism 66 extends along the length of the rotary shaft 62. The speed change mechanism 66 includes a first portion (first gear 38) and a second portion (second gear 42) spaced apart from each other along the rotary shaft 62. The first portion (first gear 38) of the speed change mechanism 66 has a first outer diameter D1, and the second portion (second gear 42) of the speed change mechanism 66 has a second outer diameter D2 different from the first outer diameter.

That is, the first and second tooth portions 56 and 58 of the rack member 36 are in a stepped shape according to the differences between the diameters D1 and D2 of the first gear 38 and the second gear 42 which are meshed with the tooth portions.

In the above-mentioned operating unit 18, for example, the operator selects any one of the first rotary roller 40 and the second rotary roller 44 and rotates them in a predetermined direction (in the direction of arrow C in FIG. 1 and FIG. 2) relative to the housing 34. By this operation, the rack member 36 inside the housing 34 is moved toward the connector 26 side (in the direction of arrow A) along the containing groove 50, accompanied by movement (retraction) of the outer tube body 14 toward the proximal side (in the direction of arrow A) of the housing 34. As a result, the stent 16 is released via the distal end of the outer tube body 14.

In contrast, the first rotary roller 40 or the second rotary roller 44 is selected after the stent 16 is released to an intermediate extent and is rotated in the direction opposite to the above-mentioned direction (in the direction of arrow D in FIG. 1 and FIG. 2). By this operation, the rack member 36 is moved in the direction (in the direction of arrow B) away from the connector 26 along the containing groove 50. This is accompanied by movement (advancement) of the outer tube body 14 toward the distal side (in the direction of arrow B) relative to the inner tube body 12, whereby the stent 16 is again contained in the inside of the outer tube body 14.

The stent delivery system 10 is basically configured as described above. Now, the operation and effect of the stent delivery system will be described below.

First, a state is assumed in which the guide wire is inserted into a lumen of a living body (for example, a blood vessel) and its distal end has been put indwelling at a lesion in the lumen of the living body in advance. Moreover, the operator connects a liquid injector (not shown) to the connector 26 disposed at the proximal end of the operating unit 18 and injects a liquid such as physiological saline from the liquid injector into the connector 26. As a result, the liquid flows to the distal side of the inner tube body 12 and the outer tube body 14 (in the direction of arrow B). Then, the liquid having reached the distal end is ejected from the distal ends of the inner tube body 12 and the outer tube body 14, whereby priming (air venting) of the inside of the inner tube body 12 and the outer tube body 14 is completed in vitro.

Next, the proximal end of the guide wire exposed in vitro is inserted into and passes through the distal end of the inner tube body 12 into the guide wire lumen and the inner tube body 12 and the outer tube body 14 are gradually advanced along the guide wire into the lumen of the living body.

After the arrival of the distal end of the outer tube body 14 in the lesion is confirmed by a contrast marker (not shown), first, the rack member 36 meshed with the first tooth portion 56 is moved to the proximal side (in the direction of arrow A) in the housing 34, accompanied by rotation of the first gear 38 with the first rotary roller 40 rotated in a predetermined direction (in the direction of arrow C). This is accompanied by gradual movement of the outer tube body 14 toward the proximal side of the operating unit 18. In this case, the second rotary roller 44 is rotated together with the second tooth portion 58 of the rack member 36 as the second rotary roller is meshed with the second tooth portion.

Next, after the movement of the distal end of the outer tube body 14 at a first linear speed under the rotating action of the first rotary roller 40 to the vicinity of the stent 16 is confirmed by the contrast marker (not shown), the operator stops the rotation of the first rotary roller 40 and rotates the adjacent second rotary roller 44 in a predetermined direction (in the direction of arrow C) which is in the same direction as that of the first rotary roller 40. By this operation, the rack member 36 meshed with the second tooth portion 58 moves toward the proximal side (in the direction of arrow A) in the housing 34 at a relatively lower speed (second linear speed) accompanied by the rotation of the second gear 42 having a smaller diameter and a smaller number of teeth than that of the first gear 38. This is accompanied by relatively slow movement of the outer tube body 14 toward the proximal side relative to the inner tube body 12. In this case, the rotating speed (first rotational speed) of the second rotary roller 44 by the operator may be the same as the rotating speed (first rotational speed) while rotating the first rotary roller 40.

That is, it is possible to move the outer tube body 14 toward the proximal side at a relatively lower speed relative to the stent 16 by switching the rotation of the first rotary roller 40 to the rotation of the second rotary roller 44 to switch the moving speed of the rack member 36 in a stage where the distal end of the outer tube body 14 approaches the stent 16.

Then, with the second rotary roller 44 further rotated, the stent 16 contained inside the outer tube body 14 starts being gradually exposed, starting from its distal portion; simultaneously, the stent starts being expanded radially outward. Then, the stent 16 comes into the state of being completely exposed from the outer tube body 14, whereby the stent is put indwelling in the lesion in the state of being expanded in the cylindrical shape.

As described above, the operating unit 18 constituting the stent delivery system 10 includes the first rotary roller 40 and the second rotary roller 44 that respectively have the first gear 38 and the second gear 42 which have different diameters. At the time of releasing the stent 16, it is possible to move the outer tube body 14 and the rack member 36 toward the proximal side (in the direction of arrow A) at a relative high speed (first linear speed) by rotating the first rotary roller 40 having the first gear 38 with a large diameter until the distal end of the outer tube body 14 reaches the vicinity of the stent 16, and meanwhile, it is possible to move the outer tube body 14 at a relatively lower speed (second linear speed) by rotating the second rotary roller 44 instead of the first rotary roller 40 after the distal end of the outer tube 14 reaches the vicinity of the stent 16. Therefore, it is possible to perform the release of the stent 16 in the single stent delivery system 10 promptly and highly accurately.

It is possible to promptly and highly accurately perform an indwelling operation of the stent 16 properly using the first and second rotary rollers 40 and 44 without depending on experience of the operator.

In addition, since it is possible to slowly move the outer tube body 14 at the time of releasing the stent 16 in a lumen of a living body, it is possible to prevent the indwelling position of the stent 16 from deviating relative to a predetermined position (lesion), thereby reliably and highly accurately indwelling the stent.

Furthermore, in the above description, the speed change mechanism 66 is configured to transmit driving force to the rack member 36 to be movable in the axial direction with first and second tooth portions 56 and 58 of the rack member 36 meshed with the first and second gears 38 and 42. However, the configuration of the speed change mechanism is not restricted thereto, and for example, the speed change mechanism may be configured such that the lower surface of the rack member and the outer peripheral surface of the rotary roller facing each other have an uneven surface (pearskin surface) which is slightly defined by projections and recesses and the rotating force of the rotary roller can be transmitted to the rack member under the abutting action of the uneven surface.

Figure 4:
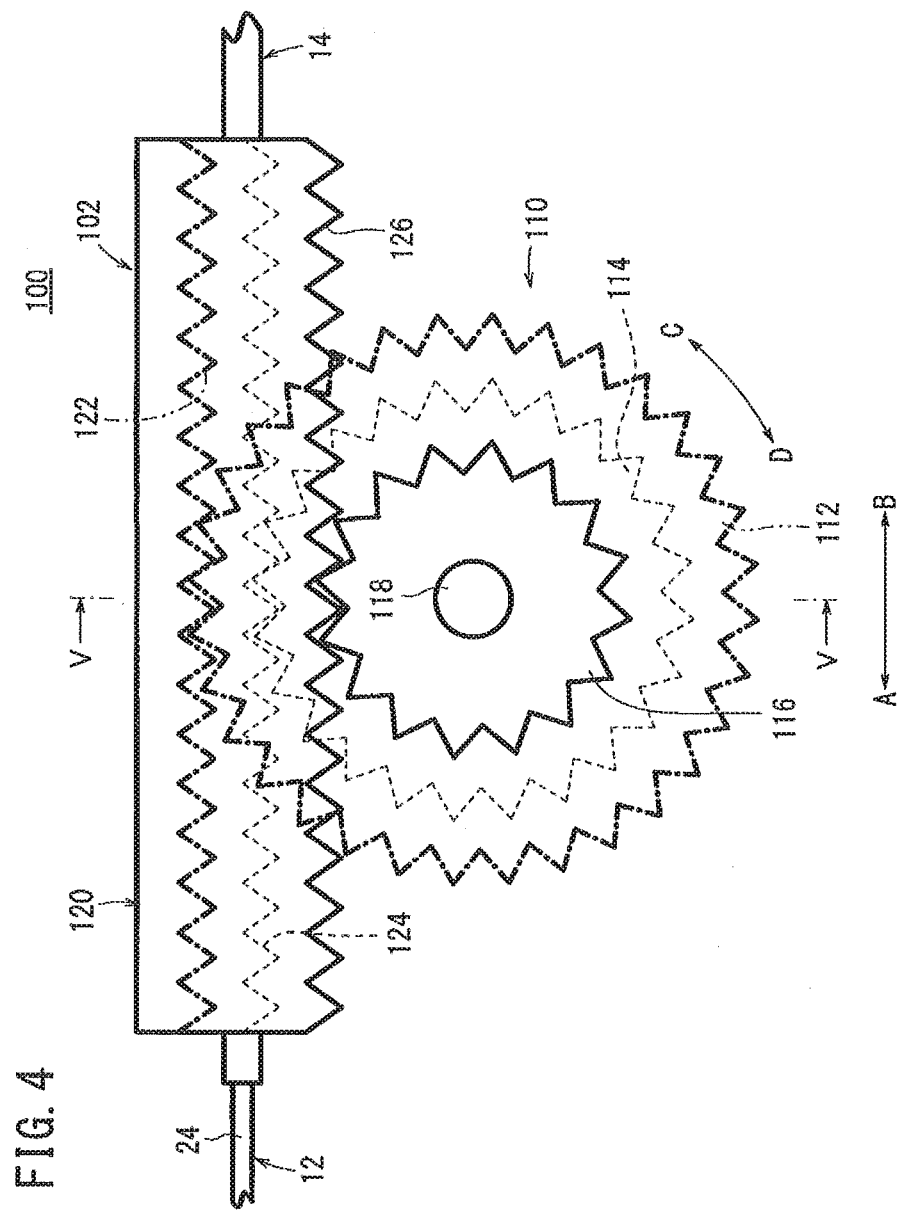
FIG. 4 is a schematic block diagram of a speed change mechanism used in an operating unit in a second embodiment of the stent delivery system representing an example of the stent delivery system disclosed here.
Figure 5:
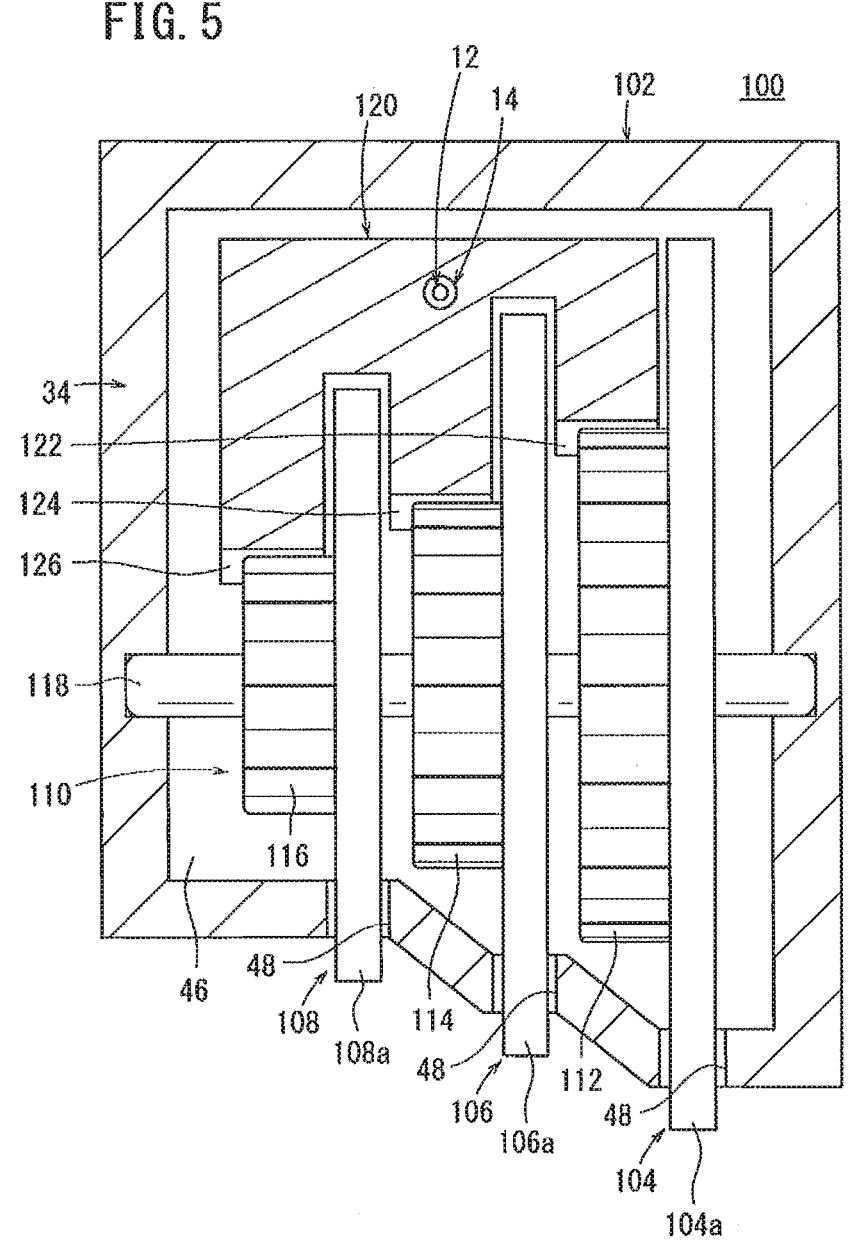
FIG. 5 is a cross-sectional view taken along line V-V of FIG. 4.

A stent delivery system 100 according to a second embodiment is shown in FIGS. 4 and 5. The same components as those of the stent delivery system 10 according to the first embodiment described above are denoted by the same reference symbols as those used above, and a detailed descriptions of such components is not repeated.

The stent delivery system 100 differs from the stent delivery system 10 in that an operating unit 102 includes a speed change mechanism 110 having 3 rotary rollers of first, second and third rotary rollers (rotary bodies) 104, 106, and 108.

As shown in FIGS. 4 and 5, the operating unit 102 constituting the stent delivery system 100 includes a first rotary roller 104 that has a first gear (speed change portion) 112 with a largest diameter; a second rotary roller 106 that has a second gear (speed change portion) 114 with a smaller diameter than that of the first gear 112; and a third rotary roller 108 that has a third gear 116 with a still smaller diameter than that of the second gear 114. The first, second and third rotary rollers 104, 106, and 108 are provided in a housing 34 so as to be rotatable based on a shaft 118 inserted into and passing through the center portion and are coaxially provided in a roller containing section 46 of the housing 34.

The first, second and third rotary rollers 104, 106, and 108 are provided so as to be separated from one another with equal intervals along the axial direction of the shaft 118. Main bodies 104*a*, 106*a*, and 108*a* are exposed to the exterior through a roller hole 48 of the housing 34 and the diameters of the main bodies 104*a*, 106*a*, and 108*a* are different from each other depending on the diameters of the first, second and third gears 112, 114, and 116. That is, the main body portion 104*a* of the first rotary roller 104 has a largest diameter and the main body portion 108*a* of the third rotary roller 108 has a smallest diameter.

As a result of this, since the amounts protruding to the exterior through the roller hole 48 of the first, second and third rotary rollers 104, 106, and 108 are different from each other, for example, the operator can accurately select the first, second and third rotary rollers 104, 106, and 108 by sensory identification of the differences of the rollers while operating the rotary rollers.

The lower surface of rack member (displacement body) 120 faces the first, second and third gears 112, 114, and 116 of the first, second and third rotary rollers 104, 106, and 108 in a stepped shape. A first tooth portion (transmission portion) 122 which is formed (positioned) in an uppermost position is formed (provided) on a part which faces the first gear 112 and a third tooth portion (transmission portion) 126 which is formed (positioned) in a lowermost position is formed (provided) on a part which faces the third gear 116. In addition, on the lower surface of the rack member 120, the second tooth portion (transmission portion) 124 faces the second gear 114 between the first tooth portion 122 and the third tooth portion 126. Moreover, the first, second and third tooth portions 122, 124, and 126 are defined by projections and recesses arranged along the axial direction (in the direction of arrows A and B) of the rack member 120 and are meshed with the first, second and third gears 112, 114, and 116, respectively.

That is, the lower surface of the rack member 120 is in a stepped shape according to the differences between the diameters of the first, second and third gears 112, 114, and 116 which are meshed with the first, second and third tooth portions 122, 124, and 126.

When performing release of the stent 16 by operating the operating unit 102 having the speed change mechanism 110 described above, after the arrival of the distal end of the outer tube body 14 in the lesion is confirmed by a contrast marker (not shown), first, the rack member 120 meshed with the first tooth portion 122 is moved toward the proximal side (in the direction of arrow A) at a high speed in the housing 34 accompanied by the rotation of the first gear 112 by rotating the first rotary roller 104 in a predetermined direction (in the direction of arrow C). This is accompanied by gradual movement of the outer tube body 14 toward the proximal side of the operating unit 102.

In this case, the second and third rotary rollers 106 and 108 are rotated together with the second and third tooth portions 124 and 126 of the rack member 120 as the second and third rotary rollers are meshed with the second and third tooth portions.

Next, after the movement of the distal end of the outer tube body 14 under the rotating action of the first rotary roller 104 toward the stent 16 by a predetermined distance is confirmed by the contrast marker (not shown), the operator stops the rotation of the first rotary roller 104 and rotates the adjacent second rotary roller 106 in a predetermined direction (in the direction of arrow C) which is in the same direction as that of the first rotary roller 104.

By this operation, the rack member 120 meshed with the second tooth portion 124 moves toward the proximal side (in the direction of arrow A) at a relative low speed compared to the rotation of the first rotary roller 104 accompanied by the rotation of the second gear 114 having a smaller diameter and the smaller number of teeth than those of the first gear 112. This is accompanied by relatively slow movement of the outer tube body 14 toward the proximal side relative to the inner tube body 12. In this case, the rotating speed of the second rotary roller 106 operated by the operator may be the same as the rotating speed while rotating the first rotary roller 104.

After the movement of the distal end of the outer tube body 14 under the rotating action of the second rotary roller 106 to the vicinity of the stent 16 is confirmed again by the contrast marker (not shown), the operator stops the rotation of the second rotary roller 106 and rotates the adjacent third rotary roller 108 in a predetermined direction (in the direction of arrow C) which is in the same direction as that of the first and second rotary rollers 104 and 106.

By this operation, the rack member 120 meshed with the third tooth portion 126 moves toward the proximal side (in the direction of arrow A) in the housing 34 at a still lower speed accompanied by the rotation of the third gear 116 having a still smaller diameter and a still smaller number of teeth than those of the second gear 114. This is accompanied by still slower movement of the outer tube body 14 toward the proximal side relative to the inner tube body 12. In this case, the rotating speed of the third rotary roller 108 operated by the operator may be the same as the rotating speed while rotating the first and second rotary rollers 104 and 106.

That is, by gradually switching to the rotation of the first rotary roller 104, the rotation of the second rotary roller 106, and the rotation of the third rotary roller 108, it is possible to gradually decrease the moving speed of the rack member 120 as the distal end of the outer tube body 14 approaches the stent 16, whereby the outer tube body 14 approaches the stent 16 at a relatively lower speed even when the operator rotates the first, second and third rotary rollers 104, 106, and 108 at the same rotating speed as each other.

Then, with the third rotary roller 108 further rotated, the stent 16 contained inside the outer tube body 14 starts being gradually exposed, starting from its distal portion; simultaneously, the stent starts being expanded radially outward. Then, the stent 16 comes into the state of being completely exposed from the outer tube body 14, whereby the stent is put indwelling in the lesion in the state of being expanded in the cylindrical shape. By this operation, since it is possible to move the outer tube body 14 toward the proximal side at three different moving speeds at the time of releasing the stent 16 in a lumen of a living body, it is possible to release the stent 16 promptly and highly accurately.

The speed change mechanism 110 which includes the first, second and third rotary rollers 104, 106, and 108 having the first, second and third gears 112, 114, and 116 formed to have three different diameters and which can change the moving speed of the rack member 120 and the outer tube body 14 in three stages was described in the above description, and the configuration of the speed change mechanism is not restricted thereto. The moving speed of the rack member 120 and the outer tube body 14 may be changed in further multiple stages by providing gears having four or more different diameters.

A stent delivery system 150 according a third embodiment is shown in FIGS. 6 to 8B. The same components as those of the stent delivery system 10 according to the first embodiment described above will be denoted by the same reference symbols as those used above, and a detailed descriptions of such components is not repeated.

The stent delivery system 150 differs from the stent delivery system 10 in that an operating unit 152 includes a speed change mechanism 166 that selectively meshes a single rotary roller (rotary body) 164 having first and second gears (speed change portions) 160 and 162 relative to a rack member (displacement body) 158 having a set of first and second tooth portions (transmission portion) 154 and 156.

As shown in FIGS. 6 to 8B, the operating unit 152 constituting the stent delivery system 150 is provided with a rotary roller 164 in a housing 34 so as to be rotatable through a shaft 168 inserted into and passing through the center portion. One side surface of the rotary roller 164 is provided with a first gear 160 having a plurality of gear teeth and the other side surface of the rotary roller 164 is provided with a second gear 162 having a smaller diameter and fewer gears than those of the first gear 160. The first and second gears 160 and 162 are coaxially provided with the shaft 168 as a central axis. In addition, the rotary roller 164 is provided (positioned) inside the housing 34 through the shaft 168 so as to be movable in the axial direction of the shaft 168 (directions of arrows E and F).

As shown in FIGS. 7A and 7B, the rack member 158 has an U shape cross-section opening downward and a main body portion 164a of the rotary roller 164 is inserted into (positioned in) the space of the center of the rack member 158.

In addition, a lower surface of one end portion orthogonal to the axial direction (in the direction of arrows A and B) of the rack member 158 has a first tooth portion 154 and is defined by projections and recesses arranged along the axial direction (in the directions of arrows A and B) of the rack member 158. Moreover, the first tooth portion 154 is configured to be meshed with the first gear 160 of the rotary roller 164.

In contrast, the other end portion orthogonal to the axial direction of the rack member 158 is provided with the second tooth portion 156 which is provided so as to be substantially parallel to the one end portion of the rack member 158 and in which the lower surface of the other end portion is formed (positioned) downward relative to the lower surface of the one end portion and is defined by projections and recesses arranged along the axial direction. The second tooth portion 156 is configured to be meshed with the second gear 162 of the rotary roller 164.

As shown in FIG. 7A, when the rotary roller 164 is moved toward the one end portion side of the rack member 158 (in the direction of arrow E) through the shaft 168, the first tooth portion 154 is meshed with the first gear 160. In contrast, as shown in FIG. 7B, when the rotary roller 164 is moved toward the other end portion side of the rack member 158 (in the direction of arrow F) through the shaft 168, the second tooth portion 156 is meshed with the second gear 162. That is, with the rotary roller 164 moved along the axial direction of the shaft 168 (in the directions of arrows E and F), it is possible to switch the meshed state of the first and second gears 160 and 162 relative to the rack member 158.

When performing release of the stent 16 by operating the operating unit 152 having the speed change mechanism 166 described above, first, the arrival of the distal end of the outer tube body 14 in the lesion is confirmed by a contrast marker (not shown). Then, as shown in FIGS. 7A and 8A, the rotary roller 164 is moved toward the one end portion side of the rack member 158 (in the direction of arrow E) along the shaft 168 and the first gear 160 is meshed with the first tooth portion 154 to rotate the rotary roller 164 in a predetermined direction (in the direction of arrow C). By this operation, the rack member 158 meshed with the first tooth portion 154 is moved toward the proximal side (in the direction of arrow A) in the housing 34 accompanied by the rotation of the first gear 160. This is accompanied by gradual movement of the outer tube body 14 toward the proximal side of the operating unit 152.

Next, after the movement of the distal end of the outer tube body 14 under the rotating action of the rotary roller 164 to the vicinity of the stent 16 is confirmed by the contrast marker (not shown), the operator stops the rotation of the rotary roller 164, and as shown in FIGS. 7B and 8B, the rotary roller 164 is moved to the other end portion side (in the direction of arrow F) from one end portion of the rack member 158 along the shaft 168, whereby the second gear 162 is meshed with the second tooth portion 156 of the rack member 158.

Then, the rotary roller 164 is rotated in a predetermined direction (in the direction of arrow C) which is in the same direction as the above-mentioned direction. By this operation, the rack member 158 meshed with the second tooth portion 156 is moved to the proximal side (in the direction of arrow A) at a relatively lower speed in the housing 34 accompanied by the rotation of the second gear 162 having a smaller diameter and the smaller number of teeth than those of the second gear 162. This is accompanied by the movement of the outer tube body 14 toward the proximal side at a relatively lower speed relative to the inner tube body 12. In other words, even with the rotary roller 164 rotated at an equal speed, a moving speed difference between the rack member 158 and the outer tube body 14 occurs due to the difference of the number of teeth (of the diameter) between the first gear 160 and the second gear 162.

That is, it is possible to move the outer tube body 14 toward the proximal side at a relatively lower speed relative to the stent 16 by switching the meshed state of the rack member 158 relative to the rotary roller 164 between the first gear 160 and the second gear 162 in a stage where the distal end of the outer tube body 14 approaches the stent 16 and by decreasing the moving speed of the rack member 158.

Then, with the rotary roller 164 further rotated, the stent 16 contained inside the outer tube body 14 starts being gradually exposed, starting from its distal portion; simultaneously, the stent starts being expanded radially outward. Then, the stent 16 comes into the state of being completely exposed from the outer tube body 14, whereby the stent is put indwelling in the lesion in the state of being expanded in the cylindrical shape. By this operation, since it is possible to gradually change the moving speed of the outer tube body 14 through the single rotary roller 164 at the time of releasing the stent 16 in a lumen of a living body, it is possible to release the stent 16 promptly and highly accurately.

In addition, a speed change mechanism 200 in accordance with another embodiment as shown in FIGS. 9A and 9B may be used in an operating unit 204 of a stent delivery system 202.

The speed change mechanism 200 includes a first gear (speed change portion) 210 provided inside a housing 206 and on a side surface of a rotary roller (rotary body) 208; a second gear (speed change portion) 212 provided in a shaft 62 which is inserted into and passes through (positioned in) the center of the rotary roller 208; and a transmission gear (transmission body) 214 which is selectively meshed with any one of the first and second gears 210 and 212. The transmission gear 214 is meshed with a tooth portion (not shown) of a rack member (displacement body) 220. The first gear 210 has a larger diameter than that of the second gear 212 and a number of teeth of which are larger than that of the second gear 212. The first gear 210 and the second gear 212 are coaxially provided with the shaft 62 as a center.

The transmission gear 214 includes a driving side gear portion 218 which is provided so as to be rotatable about a rotary shaft 216 orthogonal to the shaft 62 and meshed with the first and second gears 210 and 212; and a driven side gear portion 222 meshed with the rack member 220. The transmission gear 214 moves between the first gear 210 and the second gear 212 under the switching action due to a switching unit (not shown) and is meshed with any one of the first gear 210 and the second gear 212.

In addition, the surface of the rack member 220 meshed with the transmission gear 214 is made to be an inclined surface which is inclined along the moving direction of the transmission gear 214.

Next, a case where the rack member 220 and the outer tube body 14 are moved along the axial direction using the speed change mechanism 200 described above will be described.

First, in a case where the distal end of the outer tube body 14 needs to approach the stent 16 and the rack member 220 and the outer tube body 14 are moved at a relative high speed within the housing 206, by setting a state where the transmission gear 214 is meshed with the first gear 210 as shown in FIG. 9A, the rotation of the rotary roller 208 is transmitted to the rack member 220 through the first gear 210 and the transmission gear 214, whereby the rack member 220 moves along the axial direction.

In a case where the distal end of the outer tube body 14 reaches the vicinity of the stent 16 and the rack member 220 and the outer tube body 14 are moved at a relative low speed, as shown in FIG. 9B, the transmission gear 214 is moved toward the second gear 212 from the first gear 210 in an oblique direction using the switching unit (not shown) and is meshed with the second gear 212 through the driving side gear portion 218. Thereafter, with the rotary roller 208 rotated, the rotation of the rotary roller 208 is transmitted to the second gear 212 and the transmission gear 214 through the shaft 62. By this operation, the rack member 220 meshed with the driven side gear portion 222 of the transmission gear 214 moves at a relatively lower speed compared to when the first gear 210 is meshed with the transmission gear 214.

That is, with the provision of the first gear and the second gear 210 and 212 having different diameters (number of teeth) in the same shaft of the rotary roller 208 and the provision of the transmission gear 214 selectively meshed with the rack member 220 and any one of the first gear 210 and the second gear 212, it is possible to change the moving speed of the outer tube body 14 and the rack member 220 along the axial direction by switching the meshed state of the transmission gear 214.

Furthermore, a speed change mechanism 230 according to another embodiment as shown in FIGS. 10A and 10B may be used in an operating unit 234 of a stent delivery system 232. The speed change mechanism 230 includes a driving pulley (speed change portion) 240 which is provided inside a housing 236 and on a side surface of a rotary roller (rotary body) 238; and a transmission pulley (transmission body) 242 which is in sliding contact with an outer circumferential surface formed in a conical shape of the driving pulley 240. The upper outer circumferential surface of the transmission pulley 242 comes into sliding contact with a sliding contact surface (transmission portion) 246 of a rack member 244 (displacement body) by friction force.

The driving pulley 240 is provided on the side surface of the rotary roller 238 and is formed in a conical shape having the shaft 62 as a center. The outer circumferential surface is inclined at a predetermined angle so as to be gradually tapered in a direction away from the rotary roller 238.

The transmission pulley 242 includes a driving-side sliding-contact portion 250 which is provided so as to be rotatable about a rotary shaft 248 orthogonal to the shaft 62 and is in sliding contact with the driving pulley 240; and a driven-side sliding-contact portion 252 which is in sliding contact with the rack member 244.

In addition, the driving-side sliding-contact portion 250 is formed at an inclined angle capable of abutting the outer circumferential surface of the driving pulley 240 and the driven-side sliding-contact portion 252 is formed at an inclined angle capable of abutting the sliding contact surface 246 of the rack member 244.

Next, a case where the rack member 244 and the outer tube body 14 are moved along the axial direction using the speed change mechanism 230 described above will be described.

First, in a case where the distal end of the outer tube body 14 needs to approach the stent 16 and the rack member 244 and the outer tube body 14 are moved at a relative high speed, by setting a state where the transmission pulley 242 is in sliding contact with the driving pulley 240 in the position near the rotary roller 238 as shown in FIG. 10A and by rotating the rotary roller 238, the rotation of the rotary roller 238 is transmitted to the rack member 244 through the transmission pulley 242, whereby the rack member 244 moves along the axial direction.

Then, the transmission pulley 242 is gradually moved away from the rotary roller 238 in a state where the transmission pulley is in sliding contact with the outer circumferential surface of the driving pulley 240 through a switching unit (not shown) accompanied by gradual approach of the distal end of the outer tube body 14 to the vicinity of the stent 16 (refer to FIG. 10B). By this operation, the rotation number of the transmission pulley 242 is continuously deteriorated as the diameter of the driving pulley 240 which is in sliding contact with the transmission pulley continuously becomes small. That is, the rotation speed of the transmission pulley 242 is continuously lowered. This is accompanied by gradual deterioration (reduction) of the moving speed of the rack member 244 which is in sliding contact with the transmission pulley 242.

That is, it is possible to continuously change the moving speed along the axial direction of the outer tube body 14 and the rack member 244 with the operations that the driving pulley 240, the diameter of which becomes continuously small, is coaxially provided with the rotary roller 238, that transmission pulley 242 which can transmit the driving force of both of the driving pulley 240 and the rack member 244 is provided between the driving and the rack member, and that the transmission pulley 242 is gradually moved in a direction away from the rotary roller 238 along the outer circumferential surface of the driving pulley 240.

In other words, the speed change mechanism 230 can continuously change the moving speed steplessly along the axial direction of the outer tube body 14 and the rack member 244 under the rotating action of the rotary roller 238.

The stent delivery system is not restricted to the above described embodiments, and, naturally, various configurations are possible without departing from the gist of the invention.

The detailed description above describes a stent delivery system by way of examples. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
an inner tube;
a stent which is compressed toward a center axis and disposed on a distal side of the inner tube during insertion into a lumen of a living body, and which can be restored to a pre-compression shape by expanding outward when put indwelling in the lumen of the living body;
an outer tube which is disposed on an outer surface side of the inner tube, the outer tube containing the stent, and movable relative to the inner tube and the stent to release the stent by moving proximally relative to the inner tube; and
an operating unit operable by an operator to move the outer tube in an axial direction relative to the inner tube,
wherein the operating unit includes
a plurality of rotary bodies configured to be rotated by an operation performed by the operator,
a displacement body connected to the outer tube and movable in the axial direction, and
a speed change mechanism which is provided between the rotary bodies and the displacement body and changes a speed of the rotation of the rotary bodies, thereby changing a moving speed of the displacement body by transmitting the rotation to the displacement body, and
wherein the speed change mechanism includes
a plurality of speed change portions which have different respective outer diameters and each of which is rotated together with a respective one of the rotary bodies, said plurality of speed change portions configured to rotate at different respective speeds, and
a unitary transmission portion which is provided on the displacement body and which is meshed with or is in sliding contact with all of the speed change portions.

2. The stent delivery system according to claim 1, wherein each speed change portion is composed of a gear, the transmission portion including a plurality of tooth portions extending along an axial direction of the displacement body, a number of the gears corresponding to a number of the tooth portions, each of the plurality of gears meshing with a respective one of the plurality of tooth portions.

3. The stent delivery system according to claim 1, wherein the transmission portion is parallel to the movement direction of the displacement body and is on the surface formed in a stepped shape by facing the speed change portion.

* * * * *